Figure 1:
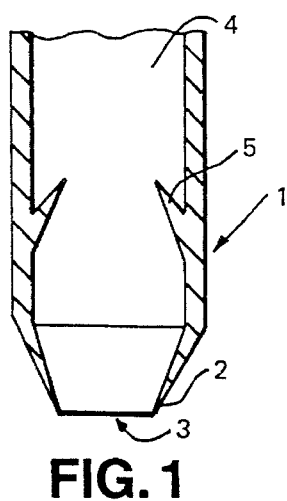

United States Patent [19]

Crowe

[11] Patent Number: 5,538,008
[45] Date of Patent: Jul. 23, 1996

[54] FORCEPS FOR ENDOSCOPES

[76] Inventor: John Crowe, 49, Ailesbury Road, Dublin 4, Ireland

[21] Appl. No.: 214,292

[22] Filed: Mar. 17, 1994

Related U.S. Application Data

[63] Continuation-in-part of PCT/IE94/00003, Jan. 17, 1994.

[30] Foreign Application Priority Data

Jan. 18, 1993 [IE] Ireland .................................. S930032
Jan. 18, 1993 [IE] Ireland .................................. S930033

[51] Int. Cl.$^6$ ..................................................... A61B 17/32
[52] U.S. Cl. .......................... 128/751; 606/170; 606/205
[58] Field of Search .................................... 128/751, 753, 128/754, 752; 606/205, 207, 206, 170, 171

[56] References Cited

U.S. PATENT DOCUMENTS

| | | | |
|---|---|---|---|
| 1,867,624 | 7/1932 | Hoffman | 128/754 |
| 3,577,979 | 5/1971 | Van Der Gaast | 128/754 |
| 4,393,872 | 7/1983 | Reznik et al. . | |
| 4,427,054 | 1/1984 | Bel et al. | 128/751 |
| 4,557,255 | 12/1985 | Goodman . | |
| 4,655,219 | 4/1987 | Petruzzi . | |

FOREIGN PATENT DOCUMENTS

| | | |
|---|---|---|
| 0065054 | 11/1982 | European Pat. Off. . |
| 0066465 | 12/1982 | European Pat. Off. . |
| 0279358 | 8/1988 | European Pat. Off. . |
| 0327410 | 8/1989 | European Pat. Off. . |
| 0380874 | 8/1990 | European Pat. Off. . |
| 0537116 | 4/1993 | European Pat. Off. . |
| 3500444 | 7/1986 | Germany . |
| WO92/11882 | 7/1992 | WIPO . |

Primary Examiner—Michael H. Thaler
Attorney, Agent, or Firm—Young & Thompson

[57] ABSTRACT

In a forceps device for use with an endoscope, two jaws are displaceable towards and away from one another for engagement and separation of a portion of tissue during a closing movement of the jaws. The jaws are formed from a resilient material at one axial end of an inner sleeve received within an outer sleeve. The jaws are biassed into a normally open configuration, which they take up when inner sleeve is axially extended outwardly from outer sleeve. Closure of the jaws is brought about by withdrawing inner sleeve axially into outer sleeve. A portion of tissue separated by the jaws is withdrawn to a retaining disposition within the device past barbs or spikes extending radially inwardly into the interior of the inner sleeve from the inner face of outer sleeve through axially extending slots in the inner sleeve in the jaw region. Once a portion of tissue has been withdrawn behind these barbs, the tissue is held by the barbs when the inner sleeve is again extended axially forward to project from the end of outer sleeve. In this manner, a succession of tissue samples may be taken for a single insertion of the forceps device into the body of a patient, the successive samples being retained within the inner sleeve. Each new sample is withdrawn past the barbs and pushes previous samples farther into the sleeve. The succession of samples is held within sleeve until the device is withdrawn from within the patient's body, at which time all of the samples may be removed from the inner sleeve, such as by blowing them out again using air pressure, for subsequent analysis. The forceps device may be provided as a disposable unit and the invention also extends to further constructions of disposable and multiple-sample endoscopic forceps.

2 Claims, 6 Drawing Sheets

FORCEPS FOR ENDOSCOPES

BACKGROUND OF THE INVENTION

1. Field of the Invention

This is a continuation-in-part application of copending International Application PCT/IE94/00003 which was filed on Jan. 17, 1994, and designated the United States of America.

The present invention relates to improvements in forceps systems for use in endoscopes.

2. Description of the Prior Art

Endoscopy is a special medical examination of the interior of the body, usually through a natural body opening, by the insertion of a tube device. Recent advances in fibre optics and in ultraminiaturized photography have greatly improved endoscopic examination of the stomach and gastro-intestinal tract, the bowels, rectum, and other internal organs. The great advantage of these techniques is that surgery is not required, or in some cases, only a minor incision is required. In conjunction with endoscopic examination, biopsy may be employed to remove tiny samples of tissue or body fluids from internal organs via a tube device. Typically, an endoscope may comprise a bundle of fibre optic cables disposed around a central passageway through which other surgical devices including, for example, cable-operated biopsy forceps, may be passed. When using a cable-operated forceps of small dimensions for endoscopic biopsy, a separate insertion and removal is required for each test. Such a procedure can be very tedious when a number of tests are in question, since endoscopic tubes may extend up to 7 feet within the body. The usual maximum diameter for the central core passageway is typically 3.2 mm., but it may be of lesser size.

Cable-operated biopsy forceps for use in an endoscope typically comprise a miniaturised tissue grip and lever mechanism at the operating end of the forceps, which is located at a forward or operating end of a sleeved-type activating cable structure, typically approximately 2 meters in length, which extends during use back through the endoscope to a handle portion gripped by the user in carrying out surgical procedures. Typically, the handle structure is provided with ring-shaped members engaged by the fingers to open and close the forceps.

BRIEF SUMMARY OF THE INVENTION

It is an object of the invention to provide an improved forceps system for use in an endoscope which will enable the retrieval of multiple samples without necessitating withdrawal of the forceps from the endoscope for release of each individual sample.

Since cable-operated biopsy forceps of the kind described above are expensive to purchase, typically costing in excess of $450.00, the present invention is therefore also directed to the provision of a disposable forceps, suitable for a single use or series of uses on an individual patient and subsequent discarding.

According to a first aspect of the invention, there is provided a forceps system for use in an endoscope, comprising a tissue-separating portion and a duct having a first end region located substantially at said tissue-separating portion and a second end region which may be located remotely from said tissue-separating portion, said duct serving for transfer of tissue portions separated by said tissue-separating portion and released by said portion for entry into said duct, from said first end region of the duct to said second end region, for retrieval in use of the system.

In a first variant of the invention in this aspect, said duct may be defined by a passage of an endoscope. Suitably, the system comprises means for effecting a tissue-separating operation of said tissue-separating portion, and said operation-effecting means may comprise at least one member extending through said passage of the endoscope defining said duct. Alternatively, said operation-effecting means may comprise at least one member extending through another passage of the endoscope.

In a favoured embodiment of the forceps system of this aspect of the invention, said duct is defined by a tube insertable through a passage of an endoscope. In an especially favoured arrangement, said tube is accommodated within a sleeve, said sleeve and tube being together insertable through a passage of an endoscope. Preferably, said sleeve is of generally circular cross-section and said tube accommodated with said sleeve has a cross-section defining at least one flow passage between said tube and sleeve. In a particularly favoured embodiment of this aspect of the invention, said tube is also of generally circular cross-section having at least one flat portion to define said at least one flow passage.

In the sleeved variant of the first aspect of the invention, said first end region of said tube may comprise a plurality of jaws defining said tissue-separating portion and a tissue-separating operation is executed by effecting relative axial displacement of said tube and said sleeve. In general, said tissue-separating portion suitably comprises said first end region of said tube, and said first end region of said tube may further comprise at least one cutting edge. In a variety of arrangements according to the invention in its first aspect, said first end region of said tube may comprise a plurality of jaws, as particularly favoured for the sleeved duct construction already described.

In an alternative construction, said tissue-separating portion may comprise a cutter located at said first end region of said tube. Means are then suitably also provided for effecting a tissue-separating operation of said tissue-separating portion, said operation-effecting means comprising, for example, at least one member extending through said duct to said cutter.

Said transfer of tissue portions separated by said tissue-separating portion through said duct may be effected by vacuum means of the system of the invention, in a first embodiment of this feature of the invention. Alternatively, in a favoured arrangement, the system of the invention may comprise pressure means for effecting said transfer of tissue portions separated by said tissue-separating portion through said duct. Said pressure means may comprise means for providing a supply of water under pressure at said first end region of the duct for establishing a flow of water through said duct towards said second end region to entrain in said flow tissue portions separated by said tissue-separating portion and thereby effect said transfer of said tissue portions.

The invention in this first aspect extends not only to a forceps system substantially as described herein with reference to and as shown in any one or more of the accompanying drawings, but also to an endoscopic system comprising any of the features of the forceps system as previously described, as well as an endoscope provided with a forceps system incorporating the features of the invention.

Advantages of the invention in its first aspect are the ability to take samples within the human body for return to the exterior without necessarily withdrawing the biopsy device. The samples are conveyed along the duct communicating between the separating or jaw region of the device and the exterior, either by vacuum or by pressurised water flowing from the inner end of the device outwards. In either case, the same principle applies—namely the samples are entrained in an outward flow for retrieval at the external end of the duct of the system.

According to a second aspect of the invention, there is provided a forceps device for use with an endoscope, comprising at least two jaws displaceable towards and away from one another for engagement and separation of a portion of tissue during a closing movement of the the jaws, and means for effecting displacement of the jaws between an open disposition and a closed disposition, wherein the jaws and at least a jaw-carrying portion of the forceps device comprise a single integral structure.

Suitably, said jaws are biassed towards an open disposition, while said jaw-carrying portion preferably comprises a shank from which said jaws extend. Said means for effecting displacement of the jaws between an open disposition and a closed disposition may then comprise a sleeve within which said shank is received, means being provided for displacing said shank relative to said sleeve, so that said jaws are forced towards one another by withdrawal of the shank into the sleeve.

In one embodiment of the invention in this second aspect, said sleeve is defined by a tubular portion of an endoscope within which the forceps device is accommodated. Alternatively, and in a particularly favoured embodiment of the invention, said sleeve extends between said shank and an operating handle structure for effecting displacement of said jaws between said open disposition and said closed disposition.

Said shank displacing means suitably comprises an elongate member extending between said shank and an operating handle structure for effecting displacement of said jaws between said open disposition and said closed disposition. In one embodiment of the invention, said elongate member is a rod, while in an alternative and preferred construction, the elongate member may be a hollow tubular member.

An especially favoured embodiment of the invention comprises two jaws, and it is further especially preferred that said jaws and said jaw-carrying portion are formed from a plastics material.

The integral structure of the jaw carrying portion and jaws provided by the invention facilitates embodiment of the invention in a disposable form. The further structure in which the jaws are biased towards an open disposition and are brought into a closed configuration by a relative sliding action of a jaw-carrying shank within a sleeve, closing being effected by the jaws being withdrawn into the sleeve, provides an especially effective and functional arrangement for securing the required forceps action. The sleeve may be defined by an end region of the endoscope itself, or alternatively, the sleeve may extend through a passage within the endoscope from the functional or forward end of the apparatus to an operating handle external of the patient in use of the endoscope. The displacement of the shank may be effected by means of a flexible rod extending through this tube or sleeve or through the endoscope as the case may be, or, in an alternative variant, the shank operating member may itself be tubular, sliding within the outer tube or sleeve or the outer structure defined by the passage through the endoscope. A particularly favoured embodiment of the invention in its second aspect which is especially suited to the provision of a disposable unit comprises just two jaws, operating in opposition to one another, although a multi-jaw structure, and in particular, a four-jaw structure, may also be envisaged. An economic disposable structure is facilitated by forming at least the jaws and the jaw-carrying portion from a plastics material. Preferably however, the entire structure, including sleeves and tubes, is also formed from plastics, as is the flexible rod where present. In this manner an economical disposable or throw-away construction may be achieved. Suitable forceps action is achieved as required by providing sharpened edges on the opposing edges of the plastics jaws.

According to the invention in a third aspect, there is provided a forceps device for use with an endoscope, comprising at least two jaws displaceable towards and away from one another for engagement and separation of a portion of tissue during a closing movement of the jaws, means for effecting displacement of the jaws between an open disposition and a closed disposition, and means for retaining a portion or portions of separated tissue within the device during successive tissue separating operations.

Suitably the jaws are biassed towards said open disposition. At least said jaws and a jaw-carrying portion of the forceps device may then comprise a single integral structure, preferably formed from a generally resilient material. Said means for effecting displacement of the jaws between an open disposition and a closed disposition then suitably comprises an elongate member extending between said jaw-carrying portion and an operating handle structure for effecting displacement of said jaws between said open disposition and said closed disposition. In a preferred construction of the invention in this third aspect, the elongate member is a hollow tubular member.

Said means for effecting displacement of the jaws between an open disposition and a closed disposition may then comprise a sleeve within which said jaw-carrying portion is received, means being provided for displacing said jaw-carrying portion relative to said sleeve so that said jaws are forced towards one another from a normally open disposition towards which they are biassed by withdrawal of the jaw-carrying portion into the sleeve. Said sleeve thus defines said hollow tubular member.

In one embodiment of the invention in its third aspect, said sleeve is defined by a tubular portion of an endoscope within which the forceps device is accommodated. Alternatively, and in a particularly favoured embodiment of the third aspect of the invention, said sleeve extends between said jaw-carrying portion and said operating handle structure for effecting displacement of said jaws between said open disposition and said closed disposition.

An especially favoured embodiment of the invention according to the third aspect comprises two jaws, and it is further especially preferred that at least said jaws and said jaw-carrying portion are formed from a suitable substantially resilient material.

Said jaws are suitably disposed at an axial end region or tip of a hollow tubular member or sleeve. In a favoured construction, said jaws are integral portions of said axial end or tip of said sleeve, said axial end or tip comprising said jaw-carrying portion of the device. Where said jaw-carrying portion in a hollow-tubular or sleeve-form construction is accommodated or received within a sleeve, the jaw-carrying portion accommodating or receiving portion of said sleeve thus defines an outer sleeve of the device and said jaw-carrying portion is located at an axial end or tip of an inner sleeve. Accordingly said jaw-carrying portion may comprise an axial end region of an inner sleeve received within said jaw-carrying portion-receiving sleeve, said jaw-carrying portion-receiving sleeve then defining an outer sleeve of the device.

Said means for retaining a portion or portions of separated tissue within the device during successive tissue separating operations may comprise at least one barb or like retaining member extending substantially inwardly from the inner wall surface of the outer sleeve through a respective substantially axially extending slot in the wall of said inner sleeve to engage a tissue portion engaged within said inner sleeve at least during forward axial movement of said inner sleeve relative to said outer sleeve to extend said jaw-carrying portion from within said outer sleeve towards a jaw-open configuration of the device.

Thus in an especially favoured construction, the separated portion retaining means suitably comprises a plurality of barbs or like members extending from an outer sleeve in an inward direction through slotted portions of an inner sleeve or hollow tubular member, at a tip or axial end of which jaw portions are defined. In this manner, a separated portion of tissue, once withdrawn within the inner sleeve or tube, is prevented from being again expelled or advanced during a further tissue separating operation. Alternative retaining means may also be provided, for example, either by retaining members of other configurations or by appropriate dimensioning or profiling of at least the jaw or tip region of the inner sleeve without any form of positive retention, i.e. without spikes or barbs. The possibility also exists of the retaining means being defined by the cooperative structure of the two sleeves, again without actually requiring spikes or barbs, but so that successive tissue-separating operations are not accompanied by re-advance towards the jaws of portions previously detached.

The structure in which the jaws are biased towards an open disposition and are brought into a closed configuration by a relative sliding action of a jaw-carrying shank within a sleeve, closing being effected by the jaws being withdrawn into the sleeve, provides an especially effective and functional arrangement for securing the required forceps action. As already noted, the sleeve may be defined by an end region of the endoscope itself, or alternatively, the sleeve may extend through a passage within the endoscope from the functional or forward end of the apparatus to an operating handle external of the patient in use of the endoscope. The displacement of the jaw-carrying portion is suitably effected by the jaw-carrying portion operating member being tubular, sliding within the outer tube or sleeve or the outer structure defined by the passage through the endoscope. A particularly favoured embodiment of the third aspect of the invention comprises just two jaws, operating in opposition to one another, although a multi-jaw structure, and in particular, a four-jaw structure, may also be envisaged. At least the jaws and preferably also the jaw-carrying portion are suitably formed from a suitable substantially resilient material to define a single integral structure, at least in this region of the device. At least portions of at least the sleeves and tubes may also however be formed from plastics. In this manner an economical construction may be achieved. Suitable forceps action is achieved by providing sharpened edges on opposing peripheral sections of the jaws.

Operation of the device according to the invention in its third aspect is effected in the following manner. The endoscope is inserted in the normal manner to the site of the lesion or other body tissue portion at which investigation is required. The forceps is then in turn also prepared and positioned for use. Separation of the first portion of tissue then takes place by relative displacement of the inner and outer sleeves, in the preferred embodiment described above. In this or other similar manner, the jaws are caused or allowed to initially separate, such as by virtue of outward displacement under an inherent bias provided in the jaw structure, the tip of the endoscope or forceps is located at the appropriate point and the forceps device again operated to detach a tissue portion. Withdrawal of the inner sleeve within the outer sleeve causes the jaws to close and the tissue portion to be withdrawn past the retaining barbs or spikes to a location within the inner sleeve and also rearward of the leading end or tip of the outer sleeve. The endoscope or forceps is then repositioned within the patient for the next tissue sample. Withdrawal of the endoscope or forceps from the patient's body is not required. Relative displacement of the sleeves again takes place so that the jaws are again moved forwards and open outwards into the jaw open disposition. During this forward movement of the inner sleeve relative to the outer sleeve, the barbs or other retaining means prevent the tissue portion previously detached from being again advanced and possibly lost by opening of the jaws. The jaws are then closed in the usual manner to effect a second tissue-separating operation and withdrawal of the inner sleeve within the outer sleeve again brings the separated sample back within the two tubes. Once again the barbs prevent release of this further sample when the forceps is next operated. As each successive sample is taken, it pushes previous samples back into the inner sleeve to an increasing extent. Successive samples are taken at whatever sites are required, and all samples are held within the inner sleeve until such time as the endoscope or forceps is withdrawn. Withdrawal of the forceps from the body is then followed by removal of the samples from the inner tube. This may be effected simply by applying a syringe or like expelling device to the opposite end of the tubes, and blowing the samples out by application of air pressure to be accommodated in whatever receiving vessel is positioned to accommodate them. In general, multiple samples will be taken at the site of a particular lesion. It is not usually of significance that all of the samples are intermingled for subsequent analysis, as the normal objective will be the detection of malignancy or otherwise at a particular site or lesion, rather than in any individual sample at that site or from that lesion. Regardless of how the samples are retrieved, common analysis is thus customary.

A particular advantage achieved by the present invention in its third aspect is that multiple samples may be taken for a single endoscope insertion and that these are then retained within the device for collection following final removal of the unit from the patient's body.

Figure 2:
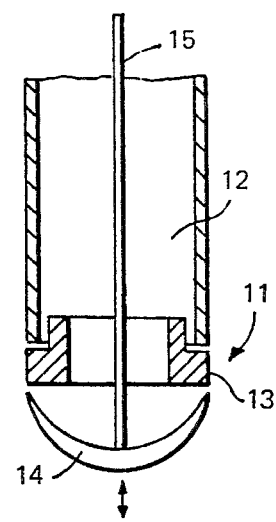
Figure 3:
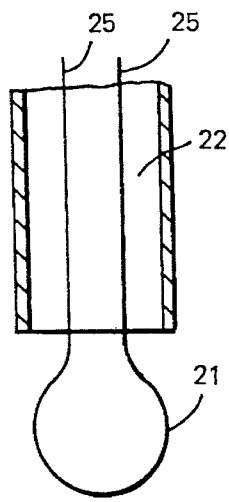
Figure 4:
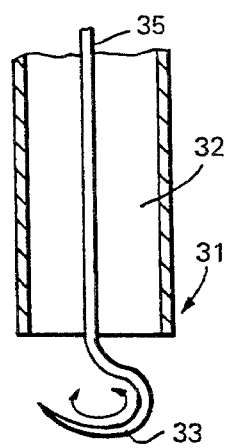
Figure 5:
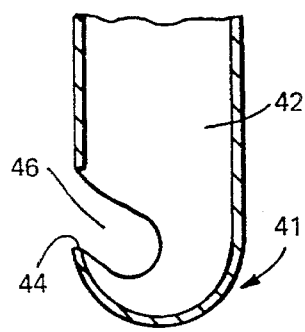
Figure 6:
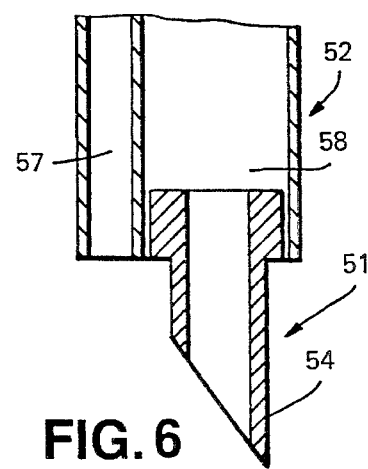
Figure 7:
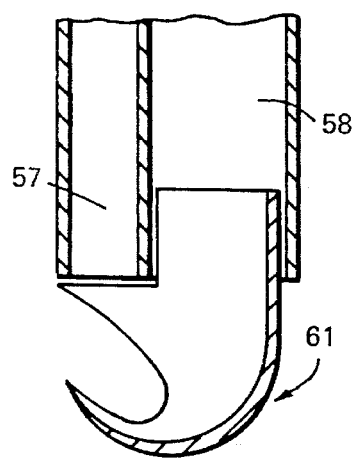
Figure 8:
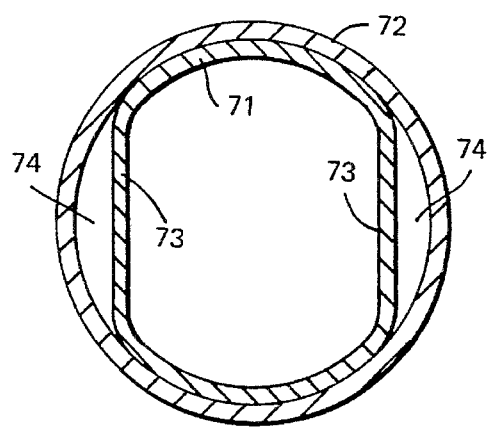
Figure 9:
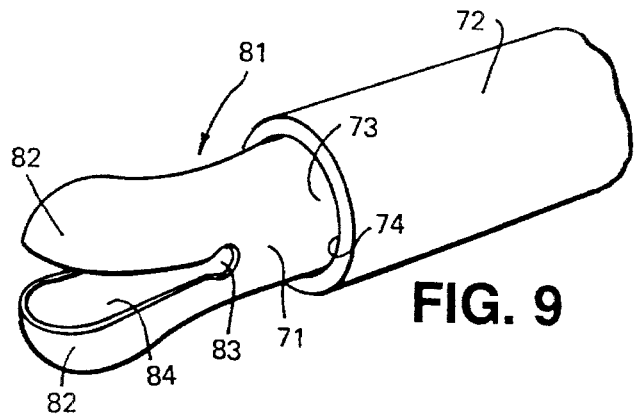
Figure 10:
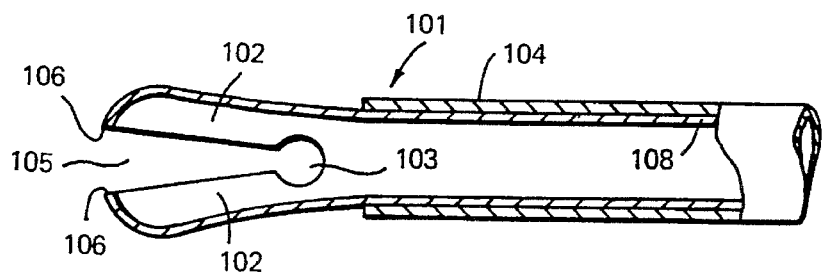
Figure 11:
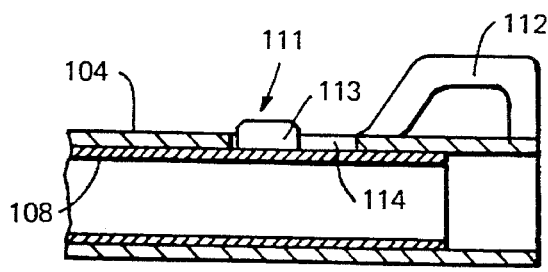
Figure 12:
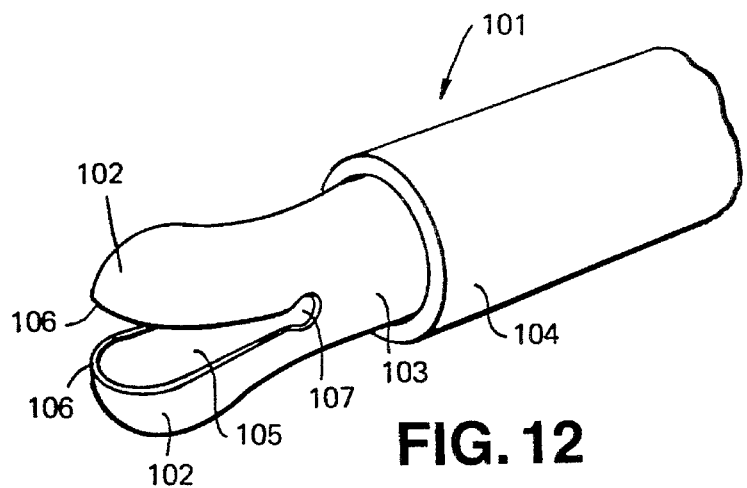
Figure 13:
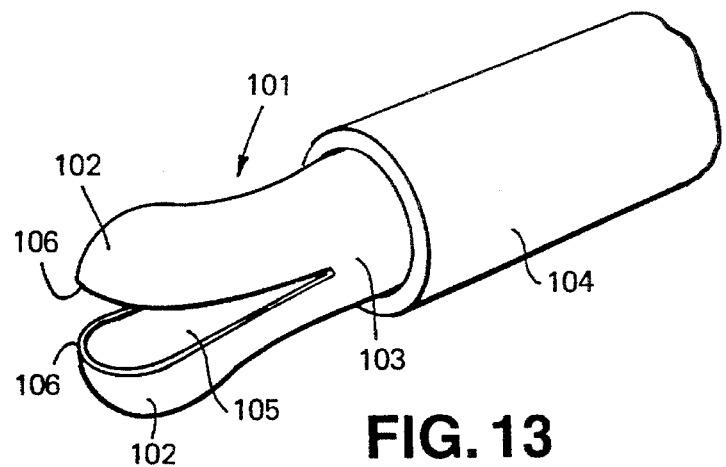
Figure 14:
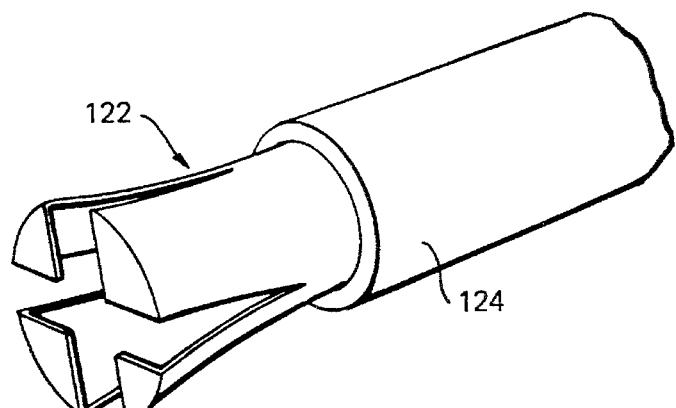
Figure 15:
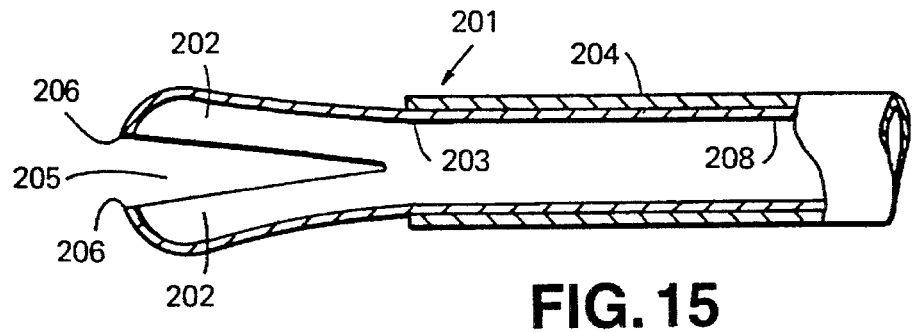
Figure 16:
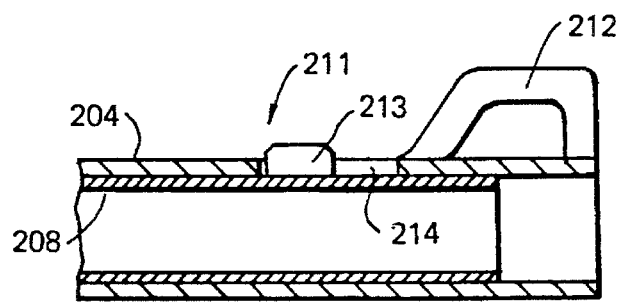
Figure 17:
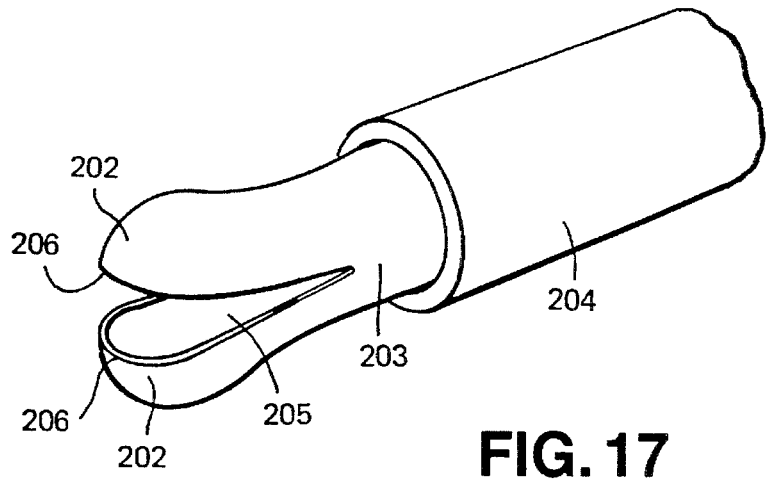
Figure 18:
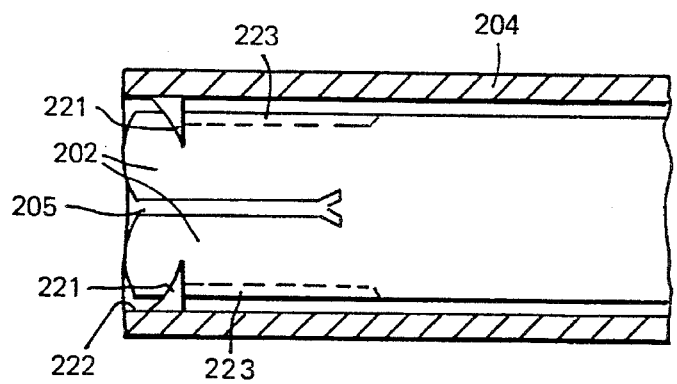
Figure 19:
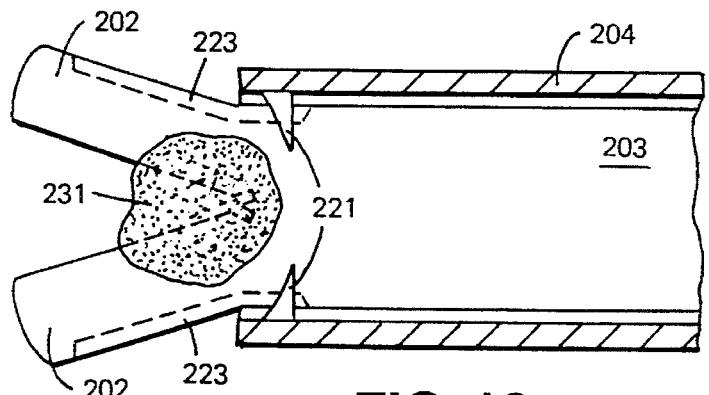
Figure 20:
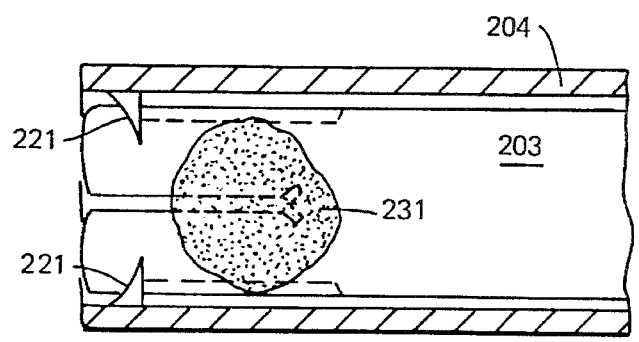
Figure 21:
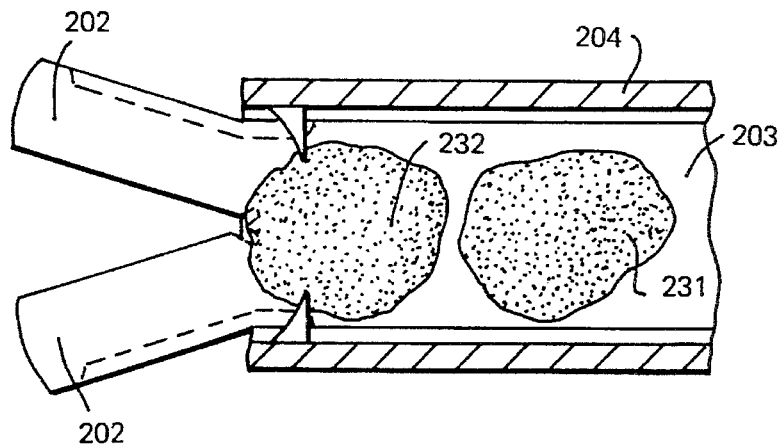
Figure 22:
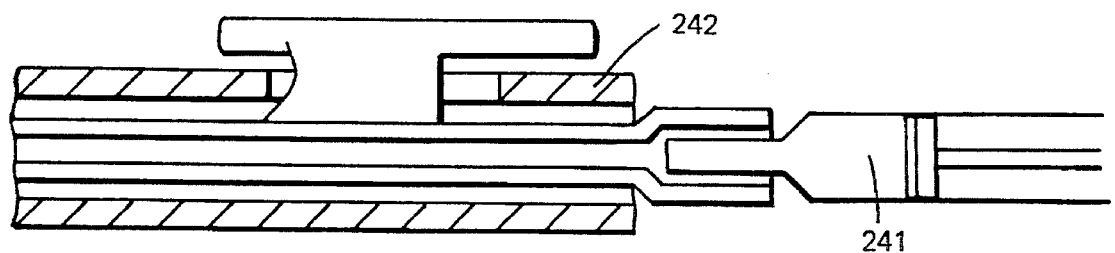

A variety of embodiments of the present invention will now be described in further detail with reference to the accompanying drawings, in which, FIG. 1 is a longitudinal cross-section, to a greatly enlarged scale, of the end of a suction biopsy tube device in accordance with the present invention in its first aspect, FIG. 2 shows an alternative biting tip for use in the system of the first aspect of the invention, FIG. 3 shows one of a diversity of sharpened wire loops usable as cutting devices within the system of the first aspect of the invention, FIG. 4 is a representation of a rotary cutter for use in a system according to the first aspect of the invention, FIG. 5 is a representation in cross-sectional view of a dragging tip type cutter for use in the system of the first aspect of the invention, FIG. 6 shows a configuration of the invention in its first aspect in which transfer of samples for collection takes place in the outward direction from the cutting tip under the action of a water flow, water being supplied to the inner or cutting end of the device by means of a separate duct or passage, FIG. 7 is a representation of a dragging cutter for use in a two-channel system of the kind shown in FIG. 6, FIG. 8 is a cross-sectional view of a sleeved duct construction of the invention in its first aspect, in which passages for inward flow of water are defined between an outer sleeve and flattened portions of an internal tube, FIG. 9 is a pictorial representation of the system of FIG. 8, showing a pair of biting jaws integrally formed on the inner or tissue-engaging end of the inner tubular member of the sleeved system, FIG. 10 is a schematic sectional view of the tissue-engaging end of a forceps device according to the second aspect of the invention along its longitudinal axis, FIG. 11 is a diagrammatic sectional enlargement of a handle construction suitable for the forceps device of FIG. 10, FIG. 12 shows in pictorial diagrammatical representation, a first embodiment of jaw structure for a forceps device according to the second aspect of the invention, FIG. 13 is a view similar to that of FIG. 12 of a second embodiment of jaw construction for a forceps device according to the invention in its second aspect, FIG. 14 shows a four-jaw construction of a jaw arrangement for a forceps device according to the second aspect of the invention, FIG. 15 is a schematic sectional view of the tissue-engaging end of a forceps device according to the invention along its longitudinal axis, FIG. 16 is a diagrammatic sectional representation of a handle arrangement suitable for the forceps device of FIG. 15, FIG. 17 shows a jaw construction for forceps device according to the invention, in a pictorial diagrammatical representation, FIG. 18 is a schematic sectional representation of the jaw end of the device of FIGS. 15 to 17, in a jaw closed and empty disposition, FIG. 19 shows the arrangement of FIG. 18, with the jaws open and the device empty, the jaws being in position to detach a tissue sample, FIG. 20 corresponds to FIGS. 18 and 19, this time showing the device shut and full, having separated and retained a single sample, FIG. 21 is a further sectional drawing equivalent to those of FIGS. 18 to 20, showing the device again open, but with multiple tissue samples retained within the sleeve, FIG. 22 is a diagrammatic representation of the manner in which samples may be expelled from the system of FIGS. 15 to 21, and FIG. 23 is an end view of the forceps jaws according to the invention, showing a modification adapted for placement or location of the forceps within a patient's body by means of a guide wire.

FIG. 1 shows the forward portion of a metal fitting 1 for attachment to the end of a biopsy tube device. A tapered, sharpened leading edge 2 is formed at the end of the fitting, which defines an opening 3 communicating with a passageway 4, which in turn communicates with the interior of the biopsy tube. Inwardly-projecting barbs 5 are provided adjacent to the opening 3, which constrict the passageway 4 and are adapted to prevent fall-back of any retrieved sample once the leading edge 2 is withdrawn from the surface of an internal body organ.

In use of the invention, the end of the device 1 is applied against the internal tissue from which the biopsy is to be taken. The cutting edge may merely rest against the tissue at the biopsy site, or alternatively, a degree of positive forward pressure may be applied to ensure that the leading edge 2 cuts into the tissue at the sampling site.

The tube extending through the endoscope, at the forward end of which fitting 1 is mounted, and which extends outwardly from the endoscope at its outer end to communicate with the external environment and associated apparatus, is suitably filled with water, for transmitting suction pulses to the leading end cutter 1 and for conveying separated biopsy samples back to the external end of the system for retrieval and examination. A pressure pulse at the external end of the system transmits a suction pulse to the cutter while it is held against tissue. A portion of tissue is thus separated and is drawn back along the water-filled tube for collection at the outer end. If the sudden pull applied by a vacuum pulse is insufficient to separate an appropriate amount of tissue, a physical movement of the cutter away from the tissue may also be carried out simultaneously with the pulse. Thus the pulse alone, or pulse and pull combined, effects the desired separation of tissue. Once the sample passes into the tube, the barbs 5 prevent it from being lost from the cutter at the cutting end, by virtue of a non-return action. Continued suction draws the sample back to the outer end for retrieval. A succession of samples may be withdrawn through a single tube, each being detached by the same cutter, but individually retrieved and identified at the outer end. In this way, a number of biopsies may be carried out for a single insertion of the biopsy device, as compared with a mechanical forceps-type biopsy device, where repeated withdrawals of the forceps are required to individually retrieve each sample.

The arrangement shown in FIG. 1 represents one exemplification of a suction tip, in which samples are drawn into the duct through a small diameter opening at the leading end of the duct and cut from a larger body of tissue, as the sample expands to fill the chamber defined within the mouth of the duct to the rear of the cutting edge 2, this chamber having a larger diametral dimension than the cutting edge opening 3.

FIG. 2 shows an alternative cutting arrangement, comprising a biting tip 11 received at the end of a duct 12 for communicating with the environment externally of the endoscope. Biting tip body portion 13 is tightly engaged in the end opening of duct 12, the apparent clearances shown between these components in FIG. 2 being for clarity of representation only. Cutter 14 is operated mechanically from the external end of the forceps system by a wire or rod 15 passing through duct 12 from an exterior operating or manipulation location. Thus, the sample is cut mechanically, and suction is relied upon only as a means of retrieving the sample rather than also itself effecting the cutting action.

FIG. 3 is a representation of a cutting arrangement in which sample separation is achieved using a sharpened wire loop 21 or like member, defined at the internal or leading end of an activating member 25 extending through duct 22. As shown, activating member 25 comprises a dual wire structure. A diversity of cutter arrangements operating on the same general principle as that shown in FIG. 3 may be provided. Alternative arrangements include open loop cutters, helical cutters, and hook-shaped cutters, while single- or double-wire activating arrangements may also be deployed, as appropriate.

FIG. 4 shows a cutter 31 having a tip 33 using a rotary action to separate samples from the tissue body. Again, the rotary cutter 31 is defined at the internal end of an activating member 35 in the form of a flexible rod or cable or wire extending axially through the duct 32 of the system of the invention, duct 32 itself also being flexible for insertion and feeding through an endoscope.

FIG. 5 shows an arrangement in which the cutting action is provided by a so-called dragging tip 41, in which a shaped aperture 46 provided with a cutting edge 44 is defined at the internal or leading end of the duct 42 defined in this instance by a tube extending axially through the endoscope to the interior of the patient. In use of this embodiment, samples are separated by the dragging tip and withdrawn through the tube under vacuum. The cutter arrangement shown in this Figure may be a separate component affixed to the end of the duct or alternatively the cutter may be formed integrally at the inner or functional end of the duct to be located within the patient, to thereby comprise part of the duct. A similar option applies as appropriate to the various other cutting configurations and arrangements described herein.

A disadvantage of the foregoing structures is that sample displacement along the tube or duct by means of vacuum may in certain instances be insufficiently effective to ensure reliable sample retrieval at the outer or external end of system, for a variety of reasons, including difficulties in establishing flow through a relatively small bore tube and also partial obstruction of the tube caused by the presence of an operating wire or other like member (viz. cable, rod etc.) in the case of rotary or other like cutters. Accordingly, in an alternative construction, by using a double lumen tube, withdrawal of samples may be provided for in alternative manner by virtue of directing a continuous flow of water inwards through one lumen and the samples are then entrained in a water flow exiting through a second lumen for external retrieval. An unbroken water column may thus be defined within the exit lumen for carrying samples back to a specimen or collecting jar at the exit end of the system.

As shown in FIG. 6, an arrangement of this kind provides a cutting tip 51 in which separation of a sample takes place by a needle type cutter 54 which penetrates the surface on forward movement of the device and retains a sample when withdrawn. Water flow takes place inwardly through a first lumen 57 or tube of the duct structure 52 and samples then exit entrained in the outward water flow through the exit lumen 58 of duct 52 which communicates with the cutter 51.

FIG. 7 shows a dragging tip 61 type structure incorporating the dual flow arrangement of FIG. 6. The inflow lumen is again identified by reference 57 and the exit lumen by reference 58.

FIG. 8 shows an especially favoured construction of sleeved tube, in which an inner tube 71 defines the duct through which sample retrieval takes place and this inner tube 71 is axially sleeved within a substantially concentric outer tube or sleeve member 72. In order to define a region for inward flow of water, side portions 73 of the inner or sleeved tube or duct 71 are flattened, to define passages 74 between the outer surface of the tube 71 and the inner surface of the sleeve 72. In this manner water flow is directed inwardly through these arcuate or sectoral cross-sectional regions 74 and the water flows back through the inner duct or tube 71 and entrains samples. An arrangement of this kind may be associated with any of the cutting features already described.

However, in a particularly favoured arrangement, shown in pictorial representation in FIG. 9, the inner end 81 of the inner sleeve 71 defines a jaw type structure, and a cutting action is effected by rearward axial displacement of the inner tube 71 relative to the sleeve 72 so that the outwardly-biassed jaws 82, which occupy a normally-open disposition, are thereby forced shut to grip and separate a portion of tissue. The apertured nature of the jaw region of the device, wherein apertures 83 define a termination of the axial slit 84 by means of which the jaws 82 are defined on each side of the structure, allows water flow into inner tube or duct 71 to take place in any condition of the jaws 82, whether open or closed, and thereby entrainment of samples for return to the collection end of the forceps system is achieved. As each sample commences its journey to the exit end of the inner tube 71, the jaws may be released by relative axial displacement of the inner tube 71 to extend it forwards relative to the outer sleeve 72, and thereby release the jaws preparatory to retrieval of a further sample.

Preferably, the tube and sleeve are formed from a plastics material, such as a polycarbonate plastics material. Thus a substantially rigid structure is provided over a short length of the arrangement, but in aggregate, when embodied in for example a two meter long structure for use in an endoscope, the device is sufficiently flexible to pass through the endoscope.

In further variants of the multiple-sample first aspect of the invention as shown in FIGS. 1 to 9, the duct may in fact be defined by a passage of the endoscope proper, with the tissue separating means or cutter being located at the tip or functioning end of the endoscope. Two passages of the endoscope may be employed where water flow is used to entrain and carry samples to the outer end. Where physical activation of the cutter is required, the activating means may be carried through the retrieval passage or through another passage of the endoscope.

Where the system employs a separate tubular structure, passed through the endoscope at the time of use, the forceps and sample retrieval aspects of the invention as shown in FIGS. 1 to 9 may preferably be embodied in a disposable plastics structure, such as subsequently described with regard to FIGS. 10 to 14 in respect of an alternative aspect of the invention.

In all embodiments of the system of the invention in its multiple-sample first aspect as shown in FIGS. 1 to 9 however, the primary objective of the invention is achieved, namely to provide for sample retrieval externally of an endoscope without necessarily requiring withdrawal of the forceps after each cutting or tissue-engaging action.

Referring now to FIG. 10, a forceps device 101 for use with an endoscope has two jaws 102 which are displaceable towards and away from one another in operation of the device. The jaws 102 are formed from a plastics material and form integral extensions of a shank portion 103 of the forceps unit which is received within a tubular sleeve 104. The jaws 102 are separated from one another in this construction of the device by a longitudinal slit 105 extending along the longitudinal axis of the shank portion 103 to define a diametral plane including the longitudinal axis and are given a bias into a disposition in which the cutting tips or edges 106 of the jaws 102, which are suitably sharpened, are spaced apart from one another. Closing action of the jaws 102 is achieved by withdrawing the shank 103 within the outer sleeve 104, so that closing action is effected in a collet-type manner. As shown in FIG. 10, the longitudinal slit 105 is terminated by an enlarged stress-relieving aperture 107 on each side of the generally tubular member defining the shank portion 103.

In the arrangement shown in FIG. 10, the forceps device 101 comprises a continuous sleeve 104 extending from the shank region 103 to an external or handle end of the device. Axial displacement of the shank 103 in the rearward and forward direction is effected by a longitudinal shaft 108 extending along the length of the sleeve 104 and within the sleeve between the jaws 102 and the handle structure. Again as shown in FIG. 10, the shaft 108, sleeved within sleeve 104 and sheathed by the sleeve, is itself a tubular member of the structure, i.e. it is hollow. The case of a tubular internal member 108 within sleeve 104 represents a particularly favoured construction of the invention, but the tubular shaft 108 may readily be substituted by a solid operating shaft as required or appropriate.

Operation of the forceps device 101 is extremely simple. It is inserted through an endoscope which has already been inserted into and positioned within a patient, the portion of tissue to be separated is identified, the axial shaft 108 within the sleeve 104 is pulled rearwardly relative to the sleeve, and the jaws 102 are accordingly closed about the portion of tissue in question, to separate it from the main body of tissue to which it is initially attached and engage it for retention while the forceps device 101 is withdrawn from the endoscope. The specimen may then be released from the forceps device 101 by again opening the jaws 102. This device provided by the invention in this second or disposable construction is suitably formed from plastics material and may thus provide an inexpensive and hygienic disposable forceps device as compared with the expensive metallic structures currently used. Variants may be provided on the structure described, in particular by substituting a solid internal operating shaft extending from the shank to the handle structure for the hollow shaft or tube 108 shown, which is sleeved within the outer tube or sleeve 104 of the device.

A further variant may also be provided in which the sleeve for the forceps device is defined by the leading end of a tube or passage of the endoscope itself, thus enabling the outer sleeve 104 to be dispensed with.

FIG. 11 shows in sectional schematic view a preferred handle structure 111 for use with the invention in this second aspect, in which a hand-grip 112 is connected or affixed to the outer sleeve 104, while a sliding button-type feature 113 communicates with the internal tubular shaft 108 or solid rod as appropriate for longitudinal displacement thereof through a longitudinally extending slot 114 in the wall of tubular sleeve 104.

FIG. 12 is a pictorial representation of the jaw structure shown in section in FIG. 10. FIG. 13 shows an alternative configuration of double jaw construction in which no stress-relieving aperture is present at the base of the longitudinal slit on each side of the structure. A four-jaw configuration is also encompassed within the scope of the present disposable-structure second aspect of the invention, as depicted in FIG. 14, in which a four-pronged grabber 122 is closed by means of an outer sleeve 124, which forces the prongs to close to trap the desired sample when rearward relative displacement between the grabber 122 and the sleeve 124 takes place to effect the collet-type action already described.

A variety of materials may be used in forming the cutting jaws of the invention in this aspect as shown in FIGS. 10 to 14, including as noted above, plastics. The desired resilient action is achieved in this case by an appropriate configuration of the structure and a suitable choice of plastics material. In a further variant, the jaws may be formed from a metallic material such as an appropriate grade of steel. The cutout at the hinge region of the jaws, as represented by the apertures 107 in FIGS. 10 and 12, enables smoother action in the case of all variants of embodiment of the invention in this disposable arrangement.

The disposable forceps provided by the invention in the second aspect described above in connection with FIGS. 10 to 14 may be incorporated in a multiple-sample forceps system according to the first aspect of the invention, i.e. that described in regard to FIGS. 1 to 9. The forceps system of the first aspect of the invention may thus comprise a forceps device according to the second aspect, and the forceps device of the second aspect may be comprised in the system of the first aspect.

As shown in FIG. 15, a forceps device 201 for use with an endoscope has two jaws 202 which are displaceable towards and away from one another in operation of the device. The jaws 202 are formed from a resilient material and form integral extensions of an inner sleeve 203 of the forceps unit which is received within an outer tubular member or sleeve 204. The jaws 202 are separated from one another by a longitudinal slit 205 extending along the longitudinal axis of the jaw-carrying portion of sleeve 203 to define a diametral plane including the longitudinal axis. The jaws are given a bias into a disposition in which the cutting tips or edges 206 of the jaws 202, which are appropriately sharpened, are spaced apart from one another. Closing action of the jaws 202 is achieved by withdrawing the inner sleeve 203 within the outer sleeve 204, so that closing action is effected in a collet-type manner. Alternative jaw structures may however also be provided within the context of the invention.

Sleeve 204 is suitably continuous and extends from the jaw region to an external or handle end of the device. Sleeve 204 comprises a suitable resilient material to provide a flexible tubular structure. Plastics may be used for sleeve 204. The jaws 202 are thus formed at a jaw-carrying portion of sleeve 203 comprising the leading axial end or tip of the sleeve. Axial displacement of inner sleeve 203 in the rearward and forward direction relative to outer sleeve 204 results in tissue-separating operations of the jaws. Inner sleeve 203 may also be continuous from the jaws to the handle, and may consist of the same resilient material as that of the jaws and jaw-carrying region, or alternatively, the sleeve may comprise more than one resilient material, that for the jaw region being different from that for the remainder of this component. Plastics may be used for at least part of the rearward sleeve portion. FIG. 16 shows in sectional schematic view, a handle arrangement 211 for use with the forceps of FIG. 15, in which a handgrip 212 is connected or affixed to the outer sleeve 204, while a sliding button-type feature 213 communicates with the internal sleeve 203 for longitudinal displacement thereof. Button feature 213 projects outwardly through a longitudinally extending slot 214 in the wall of the tubular sleeve 204. FIG. 17 is a pictorial representation of the jaw structure shown in section in FIG. 15.

Referring now to FIG. 18, the further particular feature of the present invention by which samples, once separated from tissue, are retained within the inner sleeve 203, is shown in this sectional representation. Spikes or barbs 221 extend inwardly from the inner wall 222 of the outer sleeve 204 through axial slots 223 in the jaw wall region 202 of the inner sleeve 203. These spikes 221 retain samples, once withdrawn into the forceps unit, against subsequent ejection from the device during successive tissue-separating operations. Spikes 221 may be integral plastics mouldings in the axial end region or tip of sleeve 204.

Use of the invention will now be described having regarded to FIGS. 19 to 21 inclusive. The forceps device 201 is inserted through an endoscope which has already been put in position within a patient. When all is ready for final activation, the leading or jaw end is in the configuration shown in FIG. 18. When the portion of tissue to be separated is identified, the inner sleeve 203 within the outer sleeve 204 is pushed forward, the tissue portion 231 is engaged, as shown in FIG. 19, and inner sleeve 203 is again pulled rearwardly relative to the outer sleeve 204. The jaws 202 accordingly close about the portion 231 of tissue in question, to separate it from the main body of tissue to which it is initially attached and engage it for retention. When the inner sleeve 203 is fully withdrawn, the situation shown in FIG. 20 prevails, in which the tissue sample 231 has been pulled back within the tip or jaw end of the forceps device 1 past the barbs or spikes 221.

The next tissue-separating operation takes place in precisely the same manner. However, during forward movement of the inner sleeve 203, the initially separated tissue portion 231 is prevented from being moved forwards again by the inwardly projecting barbs 221. When the next separated tissue portion 232 is withdrawn into the tube or inner sleeve 203, it pushes the first sample 231 further up the interior of the tube. The situation is shown in FIG. 21 for samples 231 and 232 already held within the tube 203, the jaws 202 being shown in an open configuration ready for detachment of another tissue sample. Further tissue samples may also be present, farther up the sleeve 203 and further away from the jaws 202.

The manner in which separated samples may be retrieved is shown in FIG. 22. When the forceps 201 is withdrawn, a syringe or like device 241 may be attached to the other or non-jaw 242 end of the unit. A puff of air blown into the forceps by the syringe 241 then expels the retrieved samples 231, 232 etc. from the jaw end 202. The samples are blown past the barbs 221. They may be collected in any suitable vessel. Aggregation of the samples is not a disadvantage, as they are in general analysed in common in any case. Neither is any damage the samples might sustain by being blown past the barbs in any way detrimental to subsequent use and analysis of the samples.

Figure 23:
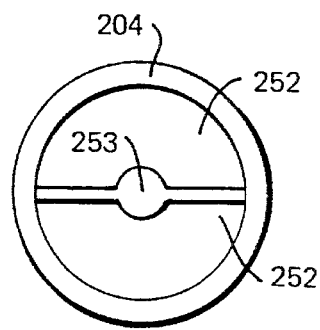

Finally, FIG. 23 is an end view showing a jaw configuration 252 in which a central recess or aperture 253 is defined between the jaw portions, through which a guidewire may pass. Use of this configuration of jaws will enable the device of the invention to be threaded over a guidewire placed endoscopically within a patient, for example within the bile duct, thereby facilitating its being put to use in similar manner to a variety of other existing devices applicable in minimally-invasive surgical operations.

Thus the invention provides an arrangement by which a number of biopsy samples may be retrieved at a single site during a single endoscope or forceps insertion and recovered when the endoscope or forceps is removed from the patient's body. The sleeved tube structure described is particularly suitable for this purpose. The forceps of the invention may thus constitute a disposable device, being manufactured in relatively simple form at least in part from plastics materials. Typically the multiple samples are taken from the same site, such as an ulcer or like lesion, internally within the body. Retention is achieved by the spikes, in the embodiment described, or other like retaining arrangements. Ten or more samples may be taken and all held within the operating tip of the device. Thus the necessity for repeated withdrawals and insertions of an endoscope or forceps is obviated by use of the invention.

I claim:

1. A forceps device for use by insertion through a fiber-optic endoscope inserted into and positioned within a patient to retrieve multiple samples without withdrawal of the forceps from the endoscope for release for each individual sample, comprising:

(a) an outer sleeve insertable through a passage of a fiber-optic endoscope, (b) an inner sleeve received within the outer sleeve, (c) a plurality of jaws located at an axial end region of the inner sleeve, (d) means for effecting axial displacement of the inner sleeve relative to the outer sleeve to force said jaws towards one another in a closing tissue-separating movement by axial withdrawal of said axial end region of the inner sleeve into the outer sleeve, and (e) a plurality of barbs for retaining portions of separated tissue within the device during successive tissue-separating operations, each barb extending substantially radially inwardly from the inner wall surface of the outer sleeve through a respective substantially axially extending slot in the wall of the inner sleeve for passage of a separated tissue portion past the barbs to a location within the inner sleeve axially rearward of the barbs during said axial withdrawal of the inner sleeve, but to prevent previously separated tissue portions at said location from being again advanced and lost by opening of the jaws during subsequent forward axial movement of the inner sleeve to open the jaws for a further tissue-separating operation.

2. A forceps device according to claim 1, wherein each barb has a sloping surface on the side thereof directed toward the jaws and a surface extending substantially at right angles to the inner wall surface of the outer sleeve on the opposite rearwardly-directed side of the barb, said sloping surface extending rearwardly from the inner wall surface of the outer sleeve towards the tip of the barb.

\* \* \* \* \*